United States Patent [19]
Kilbourn et al.

[11] Patent Number: 5,900,403
[45] Date of Patent: * May 4, 1999

[54] USE OF IRON HEMOPROTEIN FOR TREATING PATHOGENIC SYNDROME CAUSED BY NITRIC OXIDE OVERPRODUCTION

[75] Inventors: Robert G. Kilbourn, Houston, Tex.; Joseph De Angelo, Hamtramck, Mich.; Joseph Bonaventura, Beaufort, N.C.

[73] Assignees: Board of Regents, The University of Texas System, Austin, Tex.; Duke University; Apex Bioscience, Inc., both of Durham, N.C.

[ * ] Notice: This patent is subject to a terminal disclaimer.

[21] Appl. No.: 08/942,632

[22] Filed: Oct. 2, 1997

Related U.S. Application Data

[63] Continuation of application No. 08/184,255, Jan. 18, 1994, Pat. No. 5,674,836, which is a continuation of application No. 07/838,603, Feb. 19, 1992, Pat. No. 5,296,466.

[51] Int. Cl.$^6$ .................................................. A61K 38/42
[52] U.S. Cl. ................................. 514/6; 514/12; 514/21; 530/385; 424/85.2
[58] Field of Search .................................. 514/6, 12, 21; 530/385; 424/85.2

[56] References Cited

U.S. PATENT DOCUMENTS

| | | | |
|---|---|---|---|
| 4,061,736 | 12/1977 | Morris et al. | 424/177 |
| 4,584,130 | 4/1986 | Bucci et al. | 260/112 |
| 4,598,064 | 7/1986 | Walder | 514/6 |
| 4,751,068 | 6/1988 | Bickar et al. | 423/437 |
| 5,028,627 | 7/1991 | Kilbourn et al. | 514/565 |
| 5,082,642 | 1/1992 | Bickar et al. | 423/402 |
| 5,296,466 | 3/1994 | Kilbourn et al. | 514/6 |
| 5,334,706 | 8/1994 | Przybelski | 530/385 |
| 5,480,866 | 1/1996 | Bonaventura et al. | 514/6 |
| 5,510,464 | 4/1996 | Przybelski | 530/385 |
| 5,674,836 | 10/1997 | Kilbourn et al. | 514/6 |

FOREIGN PATENT DOCUMENTS

| | | |
|---|---|---|
| WO 90/02654 | 7/1990 | WIPO . |
| WO 91/04023 | 4/1991 | WIPO . |
| WO 91/04024 | 4/1991 | WIPO . |
| WO 91/84023 | 4/1991 | WIPO . |
| WO 93/00893 | 1/1993 | WIPO . |

OTHER PUBLICATIONS

Aisaka et al., "$N^G$–Methylarginine, an Inhibitor of Endothelium–DerivedNitric Oxide Synthesis, is a Potent Pressor Agent in the Guinea Pig: Does Nitric Oxide Regulate Blood Pressure in Vivo?" *Biochemical and Biophysical Research Communications*, 160(2):881–886, 1989.

Aranow et al., "Effect of Human Hemoglobin on Systemic and Regional Hemodynamics in a Porcine Model of Endotoxemic Shock," *Crit. Care Med.*, 2495):807–814, 1996.

Baur, "The Evolution of Methaemalbumin,"*Comp. Biochem. Physiol.*, 30:657–664, 1969.

Bickar et al., "Carbon Monoxide–Driven Reduction of Ferric Heme and Heme Proteins,"*Journal of Biological Chemistry*, 259(17):10777–10783,1984.

Bone, "A Critical Evaluation of New Agents for the Treatment of Sepsis," *JAMA* 266(12):1686–1691, 1991.

Bone et al., "Comparison of Different Doses of Pyridoxalatedhemoglobin Polyethylene Conjugate in the Treatment of Hyperdynamic Sepsis," *Society of Critical Care Medicine Conference, New Orleans, Feb. 5–9, 1996*.

Bone et al., "Effects of Nitric Oxide Scavenging on Sheep Pancreas and Liver During Sepsis," *Experimental Biology '96, Annual meeting of professional Research Scientists, Washington, D.C., Apr. 14–17, 1996*.

Bone et al., "Hemodynamic Effects of Nitric Oxide Synthase Inhibition and Nitric Oxide Scavenging in Endotoxemic Sheep," *International Anesthesia Research Society, 71st Clinical and Scientific Congress, San Francisco, California, Mar. 14–18, 1997*.

Bone et al., "Hemodynamic Effects of Pyridoxalated Hemoglobin Polyoxyethylene Conjugate (PHP) in Conscious Sheep During Septic Shock," *American Society of Anesthesiologist, Atlanta, 1995*.

Bone et al., "Nitric Oxide Synthase Inhibition Versus Nitric Oxide Scavenging in Sepsis," *68th Scientific Sessions of the American Heart Association, Anaheim, California, Nov. 13–16, 1995*.

Bone, "The Pathogenesis of Sepsis," *Ann. Int. Med.* 115:457–469, 1991.

Bonkovsky et al., "Intravenous Heme–Albumin in Acute Intermittent Prophyria: Evidence for Repletion of Depatic Hemoproteins and Regulatory Heme Pools," *The American Journal of Gastroenterology*, 86(8):1050–1056, 1991.

Brady et al., "Nitric Oxide Production within Cardiac Myocytes Reduces their Contractility in Endotoxemia," *Am. J. Physiol.*, 263 (*Heart Circ. Physiol. 32*):H1963–H1966, 1992.

Buga et al., "Endothelium–DerivedNitric Oxide Relaxes Nonvascular Smooth Muscle," *European Journal of Pharmacology*, 161:61–72, 1989.

Chevion et al., "Iron–NitrosylBond configuration in Nitrosyl–Hemoproteins: A Comparative EPR Study of Hemoglobin A and Hemoglobin Kansas," *Israel Journal of Chemistry*, 15:311–317, 1976.

(List continued on next page.)

*Primary Examiner*—Chhaya D. Sayala
*Attorney, Agent, or Firm*—Arnold, White & Durkee

[57] ABSTRACT

The invention is directed to a method for the prophylaxis or treatment of an animal for deleterious physiological effects such as systemic hypotension caused by nitric oxide production induced by a biological response modifier. Examples of such biological response modifiers include but are not limited to a cytokine and an endotoxin. The invention is also direction to a method for the treatment of septic shock.

16 Claims, 1 Drawing Sheet

OTHER PUBLICATIONS

Chong et al., "Determination of Methaemalbumin in Plasma," *J. Clinical Pathology*, 20:211–212, 1967.

Collier and Vallance, "Second Messenger Role for NO Widens to Nervous and Immune Systems," *Trends in PharmacologicalSciences Including Toxicological Sciences*, Elseview Science Publishers, Ltd., front page and pp. 428–431, 1989.

Cross et al., "Choice of Bacteria in Animal Models of Sepsis," *Infection and Immunity*, 61(7):2741–47, 1993.

Culotta et al., "NO News Is Good News", *Science*, 258, 1862–1865, 1992.

Finkel et al., "Negative Inotropic Effects of Cytokines on the Heart Mediated by Nitric Oxide," *Science*, 257:387–389, 1992.

Fischer, Bone and McGuire, "PyridoxalatedHemoglobin Polyoxyethylene Conjugate (PHP) Increases Effectiveness of Norepinephrine in Ovine Sepsis," *International Anesthesia Research Society, 71st Clinical and Scientific Congress, San Francisco, California, Mar. 14–18, 1997*.

Geokas et al., "Methemalbumin in the Diagnosis of Acute Hemorrhagic Pancreatitis," *Annals of Internal Medicine*, 81:483–486, 1974.

Glauser, M.P., et al. "Septic Shock: Pathogenesis," *The Lancet*, 338:732–736, 1991.

Gross et al., "Cytokine–activatedEndothelial Cells Express an Isotype of Nitric Oxide Synthase Which is Tetrahydrobiopterin–Dependent. Calmodulin–Independentand Inhibited by Arginine Analogs with a Rank–Order of Potency Characteristic of Activated Macrophages," *Biochemical and Biophysical Research Communications*, 178(3):823–829, 1991.

Gruetter et al., "Coronary Arterial Relaxation and Guanylate Cyclase Activation by Cigarette Smoke, N'Nitrosonornicotineand Nitric Oxide," *J. Pharmcology and Experimental Therapeutics*, 214(1):9–15, 1980.

Hayes et al., "Boosting oxygen Delievery Was Not Effective in Critically Ill Patients," *Annals of inernal Medicine*, 121(12):63, 1994.

Hayes et al., "Elevation of systemic Oxygen Delivery in the Treatment of Critically Ill Patients," *N Engl. J. Med.*, 330(24):1717–1722, 1994.

Ignarro et al., "Endothelium–DerivedRelaxing Factor Produced and Released from Artery and Vein is Nitric Oxide," *Proc. Natl. Acad. Sci. USA*, 84:9265–9269, 1987.

Johnston, "Molecular Science Sets Its Sights on Septic Shock," *J. NIH Res.* 3:61–65, 1991.

Kilbourn et al., "Activated Macrophages Secrete a Soluble Factor that Inhibits Mitochondrial Respiration of Tumor Cells," *The Journal of Immunology*, 133(5):2577–2581, 1984.

Kilbourne and Belloni, "Endothelial Cell Production of Nitrogen Oxides in Response to Interferon γ in Combination with Tumor Necrosis Factor, Interleukin–1, or Endotoxin," *Journal of the National Cancer Institute*, 82:772–776, 1990.

Kilbourne et al., "$N^G$–Methyl–L–arginineInhibits Tumor Necrosis Factor–Induced Hypotension: Implications for the Involvement of Nitric Oxide," *Proc. Natl. Acad. Sci. USA*, 87:3629–3632, 1990.

Kilbourne et al., "Overproduction of Nitric Oxide in Cytokine–Mediatedand Septic Shock," *J. Natl Cancer Inst.*, 84(11):827–831, 1992.

Kilbourne et al., "Reversal of Endotoxin–MediatedShock by $N^G$–Methyl–L–Arginine, an Inhibitor of Nitric Oxide Synthesis," *Biochemical and Biophysical Research Communications*, 172(3):1132–1138, 1990.

Kosaka et al., "The Interaction Between Nitrogen Oxides and Hemoglobin and Endothelium–Derived Relaxing Factor," *Free Radical Biology and Medicine*, 7:653–658, 1989.

Koshland, Jr., "Editorial—The Molecule of the Year", *Science*, 258:1861, 1992.

Kruszyna et al., "Nitrite Conversion to Nitric Oxide in Red Cells and Its Stabilization as a Nitrosylated Valency Hybrid of Hemoglobin," *The Journal of Pharmacology and Experimental Therapeutics*, 241(1):307–313, 1987.

MacMicking et al., "Altered Responses to Bacterial infection and Endotoxic Shock in Mice lacking inducible nitric oxide Synthase," *Cell*, 81:641–650, 1995.

Marden et al., "Flash Photolysis of the Serum Albumin-Heme–COComplex," *Biochemistry*, 28(10):4422–4426, 1989.

Marletta, "Nitric Oxide: Biosynthesis and Biological Significance," *TIBS*, 14:448–493, 1989.

Martin et al., "Selective Blockade of Endothelium–Dependentand Glyceryl Trinitrate–Induced Relaxation by Hemoglobin and by Methylene Blue in the Rabbit Aorta," *The Journal of Pharmacology and Experimental Therapeutics*, 232(3):708–716, 1985.

Moncada and Higgs, "Endogenous Nitric Oxide: Physiology, Pathology, and Clinical Relevance," *Eur. J. Clin. Invest.* 21:361–374, 1991.

Moncada et al. "Nitric Oxide: Physiology, Pathophysiology, and Pharmacology," *PharmacologicalReviews* 43(2):109–142, 1991.

Moncada et al., "Generation of Prostacycline and Endothelium–Derived Relaxing Factor from Endothelial Cells," In: *Biology and Pathology of Platelets—Vessel Wall Interactions*, Golles, G., Legran J.Y., and Nurden A. eds., pp. 289–304, 1986.

Moncada, et al. "The L–Arginine: Nitric Oxide Pathway," *J. Cardiovascular Pharm.* 7(Supplement3):S1–S9, 1991.

Muller–Eberhardand Morgan, "Porphyrin–BindingProteins in Serum," *Annals New York Academy of Sciences*, 224:624–649, 1975.

Mulligan et al., "Tissue injury Caused By Deposition of Immune Complexes Is L–Arginine Dependent," *Proc. Natl. Sci. Acad. USA*, 88:6338–6342, 1991.

Murray et al., "Measurement of Methaemalbumin in Plasma," *J. Clin. Path.*, 26:446–447, 1973.

Murray et al., "Stabilization and Partial Characterization of Endothelium–DerivedRelaxing Factor from Cultured Bovine Aortic Endothelial Cells," *Biochemical and Biophysical Research Communications*, 141(2):689–696, 1986.

Natanson et al., "Endotoxin and Tumor Necrosis Factor Challenges in Dogs Simulate the CardiovascularProfile of Human Septic Shock," *The Journal of Experimental Medicine*, 169:823–832, 1989.

Natanson et al., "Selected Treatment Strategies for Septic Shock Based on Proposed Mechanisms of Pathogenesis," *Annals of Internal Medicine*, 120(9):771–783, 1994.

Old, "Tumor Necrosis Factor (TNF)," 230:630–632, 1985.

Palmer et al., "Nitric Oxide Release Accounts for the Biological Activity of Endothelium–Derived Relaxing Factor," *Nature*, 327:524–526, 1987.

Palmer et al., "Vascular Endothelial Cells Synthesize Nitric Oxide from L–Arginine," *Nature*, 333:664–666, 1988.

"Panic in the Petri Dish," *The Economist*, pp. 61–62, Jul. 23, 1994.

Parratt and Stoclet, "Possible Role of Nitric Oxide in Refractory Hypotension Associated with Sepsis and Endotoxaemia and with Multiple Organ Failure," *Applied Cardiopulmonary Pathophysiology* 4:143–149, 1991.

Petros et al., "Effect of Nitric Oxide Synthase Inhibitors on Hypotension in Patients with Septic Shock," *The Lancet*, 338:1557–8, 1991.

Petros et al., "Effect of Nitric Oxide Synthase Inhibitor on Humas with with Septic Shock," *Cardiovascular Research*, 28:34–39, 1994.

Reif and Simmons, "Nitric Oxide Mediates Iron Release from Ferritin," *Archives of Biochemistry and Biophysics*, 283(2):537–541, 1990.

Rhea et al., "Vasopressor Effects of Diaspirin Cross–linked Hemoglobin (DCLHb) in Critically Ill Patients," *Crit. Care Med.*, 24(1)A39, 1996.

Ribeiro et al., "Reversible Binding of Nitric Oxide by a Salivary Heme Protein from a BloodsuckingInsect," *Science*, 260:539–541, 1993.

Sakuma et al., "Identification of Arginine as a Precursor of Endothelium–DerivedRelaxing Factor," *Proc. Natl. Acad. Sci. USA*, 85:8664–8667, 1988.

Schmidt et al., "Arginine is a PhysiologicalPrecursor of Endothelium–DerivedNitric Oxide," *European Journal of Pharmacology*, 154:213–216, 1988.

Schmidt et al., "Insulin Secretion from Pancreatic B Cells Caused by L–Arginine–Derived Nitrogen Oxides," *Science*, 255:721–723, 1992.

Snell and Parrillo, "CardiovascularDysfunction in Septic Shock," *Chest* 99(4):1000–1009, 1991.

Stamler et al., "Biochemistry of Nitric Oxide and Its Redox-ActivatedForms" *Science*, 258, 1898–1902, 1992.

Stone, "Search for Sepsis Drugs Goes on Despite Past Failures," *Science*, 264:365–367, 1994.

Stuehr et al., "Activated Murine Macrophages Secrete a Metabolite of Arginine with the Bioactivity of Endothelium–DerivedRelaxing Factor and the Chemical Reactivity of Nitric Oxide," *J. Exp. Med.*, 169:1011–1020, 1989.

Stuehr and Marletta, "Induction of Nitrite/Nitrate Synthesis in Murine Macrophages by BCG Infections, Lymphokines, or Interferon–γ," *The Journal of Immunology*, 139(2):518–525, 1987.

Stuehr et al., "Synthesis of Nitrogen Oxides from L–Arginine by Macrophage Cytosol: Requirement for Inducible and Constitutive Components," *Biochemical and Biophysical Research Communications*, 161(2):420–426, 1989.

Torti et al., "A Macrophage Factor Inhibits Adipocyte Gene Expression: An in Vitro Model of Cachexia," *Science*, 229:867–871, 1985.

Vallance et al., "Effects of Endothelium–Derived Nitric Oxide on PeripheralArteriolar Tone in Man," *Lancet*, 28:997–999, 1989.

Van Devort et al., "Nitric Oxide Regulates Endotoxin–Induced TNF–α Production by Human Neutrophils," *J. Immunol.*, 152:4102–4108, 1994.

Wang et al., Nitric oxide hemoglobin in mice and rats in endotoxic shock, *Chemical Abstracts*, 115(15):659, 1991, Abstract#. 156199a.

Westenberger et al., "Formation of Free Radicals and Nitric Oxide Derivative of Hemoglobin in Rats During Shock Syndrome," *Chemical Abstracts*, 114(21):596–598, 1991, Abstract#204845m.

Wohl et al., "Pressor Effects of Cell–Free hemoglobin in a Porcine Model of Hyperdynamic Septic Shock," *13th Annual Veterinary Forum sponsored by the American College of Veterinary Internal Medicine, May 23–26, 1996*.

Yoshida and Kasama, "Biotransformation of Nitric Oxide," *Environmental Health Perspectives*, 73:201–206, 1987.

USE OF IRON HEMOPROTEIN FOR TREATING PATHOGENIC SYNDROME CAUSED BY NITRIC OXIDE OVERPRODUCTION

This is a continuation of application Ser. No. 08/184,255, filed Jan. 18, 1994, now U.S. Pat. No. 5,674,836 which is a continuation of application Ser. No. 07/838,603, filed Feb. 19, 1992, and now U.S. Pat. No. 5,296,466.

FIELD OF THE INVENTION

The invention is directed to a method for the prophylaxis or treatment of an animal for systemic hypotension induced by a biological response modifier. Examples of such biological response modifiers include but are not limited to a cytokine and an endotoxin. The invention is also directed to a method for the treatment of septic shock.

BACKGROUND OF THE INVENTION

Endothelium-Derived Relaxing Factor

Endothelial cells have been shown to produce a potent vasodilator known as Endothelium-Derived Relaxing Factor (EDRF). Many naturally occurring substances which act as physiological vasodilators mediate all or part of their action by stimulating the release of EDRF. Examples of such substances include acetylcholine, histamine, bradykinin, leukotrienes, ADP, and ATP. Recent studies have identified EDRF as nitric oxide, a short lived, unstable compound (Ignarro et al., 1987, Proc. Natl. Acad. Sci. U.S.A. 84:9265–9269 and Palmer et al., 1987, Nature 327:524–526).

L-Arginine is the metabolic precursor of EDRF (Schmidt et al., 1988, Eur. J. Pharmacol. 154:213–216) $N^G$-methyl-L-arginine is a competitive inhibitor of the biosynthetic pathway of EDRF (Palmer et al., 1988, Nature 333:664–666). Administration of $N^G$-methyl-L-arginine to guinea pigs and rabbits has been shown to increase blood pressure (Aisaka et al., 1989, Biochem. Biophys. Res. Commun. 160:881–886). Nitric oxide (NO) appears to be synthesized from L-arginine by the enzyme, NO synthase; the coproduct is L-citrulline (Moncada et al., 1991, J. Cardiovascular Pharmacol. 17 (Suppl. 3):S1–S9). NO is an endogenous stimulator for soluble guanylate cyclase.

Nitric oxide has been found to be produced by macrophages, endothelial cells, neutrophils, Kupffer cells and hepatocytes, murine fibroblasts stimulated with cytokines, and EMT-6 cells, a spontaneous murine mammary adenocarcinoma cell line when treated with cytokine (reviewed in Moncada et al., 1991, Pharmacol. Reviews 43:109–142). Specifically, macrophage cells become activated by 12–36 hour treatments with gamma-interferon, bacterial endotoxin and various cytokines (reviewed in Collier and Vallance, 1989, Trends in Pharmacol. Sci. 10:427–431).

Endothelial cells in the presence of gamma-interferon, have been found to secrete large quantities of arginine-derived nitrogen oxides after activation by tumor necrosis factor (TNF) or endotoxin (Kilbourn and Belloni, 1990, J. Natl. Cancer Inst. 82:772–776). THF causes marked hypotension in mammals (Tracey et al., 1986, Gynecol. Obstet. 164:415–422; Old, 1985, Science 230:630–632). Additionally, THF is thought to mediate the vascular collapse resulting from bacterial endotoxin (Beutler et al., 1985, Science 229:869–871). It has recently been shown that arginine derivatives inhibit systemic hypotension associated with nitric oxide production, specifically treatment with THF, gamma interferon, interleukin-2, and bacterial endotoxin (Kilbourn et al., U.S. Pat. No. 5,028,627, issued Jul. 2, 1991; PCT Application No. WO 91/04023, published Apr. 4, 1991; and Kilbourn et al., 1990, Proc. Natl. Acad. Sci. U.S.A. 87:3629–3632). Nitric oxide overproduction is also through to be involved in numerous other pathogenic or potentially pathogenic syndromes. For example, some of these syndromes are through to be associated with malaria, senescence and diabetes. The procedures of the present invention may also be used to prevent, inhibit and/or alleviate such NO-related syndromes.

Interaction of Hemoglobin with Endothelium-Derived Relaxation Factor

Nitric oxide reacts with hemoglobin to form nitrosylhemoglobin (Kosaka et al., 1989, Free Radical Biology 7:653–658). Nitrosylhemoglobin reacts with oxygen to yield nitrate and methemoglobin, which is rapidly reduced by methemoglobin reductase. At least part of the nitric oxide is oxidized by oxygen to $NO_2$, which is in turn converted to nitrite and nitrate.

The formation of nitrosylhemoglobin has been used to quantify nitric oxide present in mice given bacterial endotoxin, specifically by using electron paramagnetic resonance (EPR) spectroscopy to detect NO liganded to hemoglobin (Wang et al., 1991, Life Sciences 49:55–60). Although bacterial endotoxin induces septic shock, hypotension was not observed in the Wang et al. Study. Those skilled in the art recognize that such EPR studies may be used to quantitate the binding of NO to other hemoproteins as well.

Hemogobin has also been found to inhibit nonvascular relaxant responses to EDRF (Buga et al., 1989, Eur. J. Pharmacol. 161:61–72). Furthermore, hemoglobin at 1 $\mu$M reduced and at 10 $\mu$M abolished the endothelium-dependent relaxation induced by acetylcholine or by A23187 in rabbit aortic rings (Martin et al., 1985, J. Pharmacol. Exp. Ther. 232:708–716). It was hypothesized by Martin et al. that the hemoglobin inhibits endothelium-dependent induced relaxation by binding nitric oxide.

Septic Shock

Septic shock is characterized by inadequate tissue perfusion and is usually caused by gram-negative enteric bacilli such as Escherichia coli, Klebsiella, Enterobacter, Pseudomonas, Serratia, and Bacteroides (see Harrison's INTERNAL MEDICINE, 10th Ed., vol. 1, Petersdorf et al., eds. McGraw Hill, N.Y. 1983). Gram-negative bacilli possess endotoxin, also known as lipopolysaccharide (LPS), which is a cell-wall component that can activate leukocytes in minute amounts in the blood.

Septic shock is characterized by chills, fever, nausea, vomiting, diarrhea, and prostration. The subsequent development of septic shock is characterized by tachycardia, tachypnea, hypotension, peripheral cyanosis, mental obtundation, and oliquria. As shock progresses, oliquria persists, and heart failure, respiratory insufficiency, and coma supervene. Death usually results from pulmonary edema, generalized anoxemia secondary to respiratory insufficiency, cardiac arrhythmia, disseminated intravascular coagulation with bleeding, cerebral anoxia, or a combination of the above.

Most of the damage caused by septic shock is thought to be caused by endotoxin. It has also been hypothesized that nitric oxide plays a major role in effecting hypotension in those exposed to endotoxin (Kilbourn et al. Biochem. and Biophys. Res. Comm. 1990, vol. 172:1132–1138). Studies have shown that the hypotension and loss of vascular responsiveness resulting from endotoxin administration is reversed by the administration of analogoues of L-arginine which inhibit nitric oxide production (Parratt and Stoclet, 1991, *Applied Cardiopulmonary Pathophysiology* 4:143–149; and Kilbourn et al., 1990, *Proc. Natl. Acad. Sci. U.S.A.* 87:3629–3632).

In certain cases, acute blood loss may cause hypotension. After initial recovery due to standard hypotension treatment, a breach of intestinal integrity may subsequently cause septic hypotension. Such a syndrome is readily treated according to the methods of the present invention.

Treatments for Septic Shock

There are currently a number of clinical procedures available for the treatment of septic shock (reviewed in Harrison's INTERNAL MEDICINE, 10th Ed., vol. 1, Petersdorf et al., eds., McGraw Hill, N.Y. 1983). However each has its drawbacks. One treatment involves the replacement of blood volume with blood plasma, or other fluids such as human serum albumin in appropriate electrolyte solutions such as dextrose saline and bicarbonate. However, large quantities of these substances are required and may amount to 8 to 12 liters in only a few hours, leading to massive shifts in fluid and electrolyte balances.

Antibiotics may also be used to treat septic shock. However, to determine the appropriate antibiotics to use, blood cultures must be taken and evaluated. Such cultures take time. Additionally, antibiotics may initially worsen shock caused by bacteria since they kill the bacteria and the dying organisms can release even more lipopolysaccharide into the body.

Vasoactive drugs such as beta-receptor stimulants (e.g. isoproterenol and dopamine) and alpha-rector blocking agents (phenoxybenzamine and phentolamine) have also been therapeutically used since septic shock is accompanied by maximal stimulation of alpha-adrenergic receptors. However, all of these drugs may have serious side effects. In addition, studies by Stoclet et al. (*Amer. J. Physiol.* 259:H1038–1043) suggest that endotoxic shock and NO production can cause lowered sensitivity to these agents, decreasing their effectiveness. The iron hemoprotein therapy of the present invention may be used to reverse this loss of sensitivity.

Another treatment approach involves using human antiserum to *E. coli* J5, a mutant strain that produces endotoxin without the variable oligosaccharide side chains. However, since such antiserum comes from many different human donors with varying immune responses to the antigen, it cannot be rigidly standardized for effectiveness. Such antiserum may also transmit infectious agents. To circumvent these problems, monoclonal antibodies that bind to endotoxin are currently being tested in patients suffering from septic shock (reviewed in Johnston, 1991, *J. NIH Res.* 3:61–65). A disadvantage of this approach is that treatment of septic patients with antiendotoxin antibodies has no immediate effect on blood pressure and may not work at all if patients are not treated at an early stage.

Another approach used to treat septic shock involves administering bactericidal permeability-increasing protein (BPI), a human protein derived from neutrophil granules. This protein binds to LPS. Versions of the molecule are currently being developed (reviewed in Johnston, 1991, *J. NIH Res.* 3:61–65).

Approaches are also being developed for treating septic shock by preventing endotoxin from activating leukocytes that start the inflammatory response (reviewed in Johnston, 1991, *J NIH Res.* 3:61–65). Examples of such approaches include administering a soluble interleukin-1 (IL-1) receptor, an IL-1 receptor antagonist, a monoclonal antibody to TNF-$\alpha$, soluble THF receptor and a monoclonal antibody to TNF-$\alpha$ receptor. All of these approaches suffer from the fact that blockade of the cytokine receptor interaction does not have an immediate effect on nitric oxide production by NO synthase (i.e.—once induced by cytokines, NO synthase continue to produce NO even after removal of the stimulus).

The present invention involves the treatment of a nitric oxide induced malady such as hypotension by administration of an iron hemoprotein which has substantial affinity for nitric oxide an/or catalyzes nitric oxide oxidation to nitrates or nitrites. The most preferred iron hemoprotein is hemoglobin, particularly recombinant hemoglobin. Myoglobin, which also is known to bind nitric oxide may also be utilized. Additional iron hemoproteins, including certain cytochromes, e.g. are known and may be used when demonstrating the above mentioned nitric oxide-related effects. Particularly preferred hemoglobins are those which have a long circulating lifetime, e.g., those which have a poor affinity for haptoglobin. Those skilled in the art will recognize that any iron heme-containing proteins or peptides binding NO may be administered to an animal in a pharmaceutically effective amount to remove nitric oxide and prevent or treat hypotension or other NO-induced deleterious effects.

Despite previous results showing the interaction of iron hemoproteins such as hemoglobin with nitric oxide, the therapeutically effective results of the present invention method are quite surprising and unexpected. Such a result could not have been expected in view of the fact that normal mammalian blood fluid is replete with hemoglobin contained in red blood cells which contain about 34% hemoglobin. Such cells usually constitute over 43% of the blood. Thus blood is about 15% hemoglobin. Additionally, nitric oxide is quite lipophilic and readily penetrates red blood cells. One skilled in the art would have expected that any effects of a free iron hemoprotein such as hemoglobin in the blood to remove deleterious nitric oxide would have been insignificant as compared to the effects of hemoglobin contained in red blood cells already present. The basis for the surprising and unexpectedly effective results of the present invention are incompletely understood at the present time, but, as the present invention is described, it will be clear to those of skill in the art that the free iron hemoproteins of the present invention such as hemoglobin are phenomenally effective or therapeutic purposes related to a reversal of deleterious physiological effects induced by nitric oxide in vivo.

SUMMARY OF THE INVENTION

The invention is directed to a method for the prophylaxis or treatment of an animal for systemic hypotension or other pathogenic syndromes induced by inappropriate nitric oxide production. Such hypotension may be induced by certain cytokines or a microbial toxin such as bacterial endotoxin. The method involves administering a therapeutically effective amount of an iron hemoprotein such as hemoglobin and the like. The administration is preferably intravascular, which includes intraarterial and intravenous. Other parenteral administration routes, e.g. peritoneal or intralymphatic, to name but a few, can be used for removal of undesired NO production at related sites. Enteral administration could be feasible if the hemoprotein or a derivative thereof was resistant to digestion and passed into the circulation. The animal may be, for example, a domestic mammal or a human patient. The systemic hypotension most characteristically results from abnormal production of nitric oxide induced by a cytokine or microbial toxin. A therapeutically effective amount of iron hemoprotein is an amount sufficient to bind and/or oxidize substantially all of the free nitric oxide and thus removing it from the circulation. In a preferred embodiment, the iron hemoprotein is hemoglobin or myoglobin and is administered intravascularly.

Bacterial endotoxin is a primary causative agent of septic shock. Elevated levels of nitric oxide have been found in animals in septic shock (Wang et al., 1991, Life Sciences 49:55–60). Therefore, the invention is also directed to a method for the treatment of septic shock in a patient comprising administering a therapeutically effective amount of an iron hemoprotein such as the preferred hemoglobin.

DETAILED DESCRIPTION OF THE INVENTION

Figure 1:
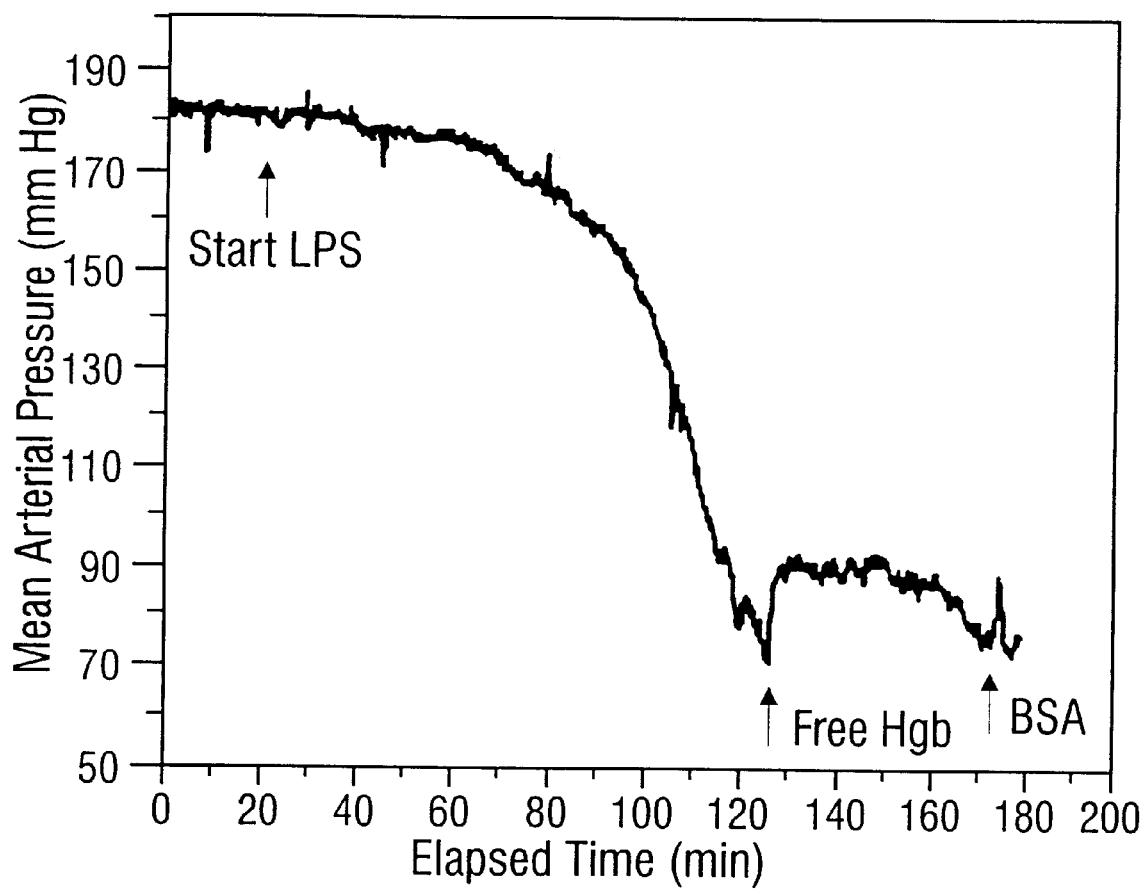
FIG. 1 shows the effect of hemoglobin on endotoxin-induced hypotension in a dog. The endotoxin-induced mean arterial decline is interrupted by administration of hemoglobin.

In a major embodiment, the present invention is directed to a method for the prophylaxis or treatment of an animal for systemic hypotension induced by a biological response modifier directly or indirectly causing nitric oxide overproduction. Examples of such biological response modifiers include but are not limited to cytokines. The invention is also directed to a method for the treatment of septic shock and associated hypotension.

Preparation of Hemoglobin

The starting material, unmodified hemoglobin, may be obtained using procedures known in the art (see for example, PCT Application Publication No. WO 88/03408, published May 19, 1988; U.S. Pat. No. 4,001,401; Feola et al., 1983, Surgery Gynecology and Obstetrics 157:399–408; De Venuto et al., 1979 Surgery Gynecology and Obstetrics 149:417–436). For example, unmodified stroma-free hemoglobin may be obtained as follows: (a) obtaining whole blood; (b) separating red blood cells from other components of whole blood; (c) isolating the hemoglobin from the erythrocytes; and (d) separating the hemoglobin from stroma and other impurities.

Stroma-free hemoglobin can be prepared by starting with erythrocytes in freshly drawn, outdated, or frozen packed cells or whole blood. The blood should be drawn in a sterile fashion into containers with sufficient anticoagulant activity to prevent clot formation.

In one embodiment, blood cells are washed in a saline solution and centrifuged to separate red blood cells from white blood cells as well as to additionally remove free proteins (Feola et al., 1983, Surgery Gynecology and Obstetrics 157:399–408). In another embodiment, the red cells may be separated from other blood cells by passing through a semi-continuous type centrifuge as described in PCT Application Publication No. WO 88/03408, published May 19, 1988.

Hemoglobin may be isolated in one embodiment by diluting the red blood cell solution in water or an organic solvent at 2–10° C. to separate the hemoglobin in red blood cells from all cell debris (PCT Application Publication No. WO 88/03408, published May 19, 1988; U.S. Pat. No. 4,001,401 Feola et al., 1983, Surgery Gynecology and Obstetrics 157:399–408). In another embodiment, the hemoglobin is precipitated as a zinc complex by the addition of a zinc salt to a hemoglobin solution (De Venuto et al., 1979, Surgery Gynecology and Obstetrics 149:417–436).

The isolated hemoglobin, in another embodiment, may be purified by ultrafiltration through for example a 0.5 micron filter which retains the cellular components and passes the hemoglobin.

Hemogobin may also be obtained through other procedures known in the art. For example, bacterial strains (see for example Nagai and Hoff man, U.S. Pat. No. 5,028,588, issued Jul. 2, 1991) or yeast (see for example PCT Application Publication No. WO90/13645, published Nov. 15, 1990), or other eukaryotic organisms may be engineered to produce hemoglobin by recombinant DNA techniques. Recombinant hemoglobin is thought to be particularly advantageous because it can be readily produced in large quantities and because utilization of such recombinant hemoglobin obviates the possibility of blood-borne infection such as that by various viruses or retroviruses.

The hemoglobin may be for example, any human hemoglobin, including but not limited to HbA (alpha$_2$beta$_2$), HbA2 (alpha$_2$delta$_2$), HbF (alpha$_2$gamma$_2$), Hb Barts (gamma$_4$), HbH (beta$_4$), and Hb Portland I (zeta$_2$gamma$_2$), Hb Portland II (Zeta$_2$beta$_2$), Hb Portland III (zeta$_2$delta$_2$) Hb Gower I (zeta$_2$epislon$_2$), and Hb Gower II (alpha$_2$epsilon$_2$); as well as any other animal hemoglobin, e.g. bovine or porcine hemoglobin.

The hemoglobin used in the method of the present invention may be chemically modified using procedures known in the art to increase tetramer stability and/or lower oxygen affinity. Examples of chemical modifications to increase the tetramer stability include but are not limited to crosslinking with polyalkylene glycol (Iwashita, U.S. Pat. No. 4,412,989 and 4,301,144), with polyalkylene oxide (Iwaske, U.S. Pat. No. 4,670,417); with a polysaccharide (Nicolau, U.S. Pat. No. 4,321,259 and 4,473,563); with inositol phosphate (Wong, U.S. Pat. Nos. 4,710,488 and 4,650,786); with a bifunctional crosslinking agent (Morris et al., U.S. Pat. No. 4,061,736); with insulin (Ajisaka, U.S. Pat. No. 4,377,512); and with a crosslinking agent so that the hemoglobin composition is intramolecularly crosslinked between lys 99 apha$_1$ and lys 99 alpha$_2$ (Walder, U.S. Pat. No. 4,598,064). Examples of chemical modifications to decrease the oxygen affinity of isolated hemoglobin include but are not limited to polymerization with pyridoxal phosphate (Sehgal et al., 1984, Surgery, 95:443–438) and using reagents that mimic 2,3-DPG (Bucci et al., U.S. Pat. No. 4,584,130).

In a further embodiment, the hemoglobin used in the method of the present invention may be a hemoglobin variant, a hemoglobin comprising a globin chain from a nucleotide sequence which has been altered in such a fashion so as to result in the alteration of the structure or function of the hemoglobin, but so that the hemoglobin still remains functionally active as defined by the ability to reversibly bind to oxygen (or nitric oxide, of course). Categories of hemoglobin variants include but are not limited to variants which autopolymerize; variants in which the tetramer does not dissociate under physiological conditions in vivo (e.g. Hb Rainer, beta-145 tyrosine is replaced by cysteine); variants with lowered intrinsic oxygen affinity, i.e. a hemoglobin having a P50 of at least about 10 mm Hg under physiological conditions (e.g. Hb Chico, beta-66 lysine is replaced by threonine; Hb Raleigh, beta-1 valine is replaced by alanine; Hb Titusville, alpha-94 aspartate to asparagine; Hb Beth Israel (beta-102 asparagine is replaced with serine; and Hb Kansas, beta-102 asparagine to threonine; variants that are stable in alkali (e.g. Motown/Hacettepe, beta-127 or glutamine is replaced with glutamic acid); variants that are stable in acid; variants which have a lowered binding affinity to haptoglobin; variants with an increase intrinsic oxygen affinity, i.e. a hemoglobin having a $P_{50}$ of at most about 1 mm Hg under physiological conditions (e.g. HbA Deer Lodge, beta-2 histidine is replaced with arginine, Labossiere et al., 1972, *Clin. Biochem.* 5:46–50; HbA Abruzzo, beta-143 histidine is replaced with arginine, Tentori et al., 1972, *Clin. Chim. Acta.* 38:258–262; and HbA McKees Rocks, beta-145 tyrosine is replaced with a termination sequence, Winslow et al., 1976, *J. Clin. Invest.* 55:772–781).

Acid stable hemoglobin variants may include those that replace the histidine at the alpha-103 position with an amino acid is not ionized in acid (Perutz, 1974, *Nature* 247:341). Examples of such amino acids include serine, threonine, leucine, and alanine.

Haptoglobin nonbinding hemoglobin variants are those with variation in the alpha-121-127 sequence. This sequence has been shown to be involved in the binding of haptoglobin which is believed incident to increased circulatory clearance (McCormick and Atorssi, 1990, *J. Prot. Chem.* 9:735).

The globin variants may be produced by various methods known in the art. The manipulations which results in their production can occur at the gene or protein level. The globin may be altered at the gene level by site-specific mutagenesis using well-known procedures. One approach which may be taken involves the use of synthetic oligonucleotides to construct variant goblins with base substitutions. In one embodiment, a short oligonucleotide containing the mutation is synthesized and annealed to the single-stranded form of the wild-type globin gene (Zoller and Smith, 1984, *DNA* 3:479–488). The resulting short heteroduplex can serve as primer for second strand synthesis by DNA polymerase. At the 5' and, a single stranded nick is formed which is closed by DNA ligase. In another embodiment, two complementary oligonucleotides are synthesized, each containing the mutant sequence. The duplex that forms after annealing these complementary oligonucleotides, can be joined to a larger DNA molecule by DNA ligase provided that the ends of both molecules have complementary single-stranded "sticky" ends. Another approach which may be taken involves introducing a small single-stranded gap in the DNA molecule followed by mis-repair DNA synthesis i.e., the misincorporation of a non-complementary nucleotide in the gap (Botstein and Shortle, 1985, *Science* 229:1193). The incorporation of a thiol nucleotide into the gap may minimize the excision of the non-complementary nucleotide. Alternatively, a globin variant may be prepared by chemically synthesizing the DNA encoding the globin variant using procedures known in the art (see for example Froehler, 1986, *Nucl. Acids Res.* 14:5399–5407 and Caruthers et al., 1982, GENETIC ENGINEERING, J. K. Setlow and A. Hollaender eds., Plenum Press, New York, vol. 4, pp. 1–17). In a preferred embodiment, fragments of the variant globin-coding nucleic acid sequence are chemically synthesized and these fragments are subsequently ligated together. The resulting variant globin-coding strands may be amplified using procedures known in the art, e.g. PCR technology, and subsequently inserted into a cloning vector as described in, e.g., PCT Application Publication No. WO90/13645, published Nov. 15, 1990). In specific embodiments, site-specific mutants may be created by introducing mismatches into the oligonucleotides used to prime the PCR amplification (Jones and Howard, 1990, *Biotechniques* 8:178–180).

Manipulations of the globin sequence may be carried out at the protein level. Any of numerous chemical modifications may be carried out by known techniques including but not limited to specific chemical cleavage by cyanogen bromide, trypsin, chymotrypsin, papain, or V8 protease, $NaBH_4$ acetylation, formylation, oxidation, reduction; etc. Alternatively, the variant globin protein may be chemically synthesized using procedures known in the art, such as commercially available peptide synthesizers and the like. Such standard techniques of polypeptide synthesis can be found described in such publications as Merrifield, 19963, *J. Chem. Soc.* 85:2149–2154 and Hunkapillar et al., 1984, *Nature* (London) 310:105–111).

Treatment of Hypotension and Septic Shock with Hemoglobin

The hemoglobin prepared according to the procedures described above may be used for the prophylaxis or treatment of systemic hypotension or septic shock induced by internal nitric oxide production. Such internal nitric oxide production may result from the treatment of an animal with a cytokine which includes but is not limited to tumor necrosis factor, interleukin-1, and interleukin-2, in the case of systemic hypotension. In a specific embodiment, hemoglobin may be used for prophylaxis or treatment of systemic hypotension in a patient induced by chemotherapeutic treatment with such cytokines. In septic shock, the production of nitric oxide results from the exposure of an animal to a bacterial endotoxin. Viral, fungal or enterotoxin-producing bacteria may also be found to directly or indirectly induce NO overproduction alleviatable by administration of the hemoproteins of the present invention.

The preferred iron hemoprotein, hemoglobin, used in the present invention is mixed with a pharmaceutically acceptable carrier. The pharmaceutical carriers are physiologically compatible buffers as Hank's or Ringer's solution, physiological saline, a mixture consisting of saline and glucose, heparinized sodium-citrate-citric acid-dextrose solution, and the like. The hemoglobin for use in the methods of the present invention can be mixed with colloidal-like plasma substitutes and plasma expanders such as linear polysaccharides (e.g. dextran), hydroxyethyl starch, balanced fluid gelatin, and other plasma proteins. Additionally, the hemoglobin may be mixed with water soluble and physiologically acceptable polymeric plasma substitutes, examples of which include polyvinyl alcohol, poly(ethylene oxide), polyvinylpyrrolidone, and ethylene oxide-polypropylene glycol condensates and the like.

Techniques and formulations for administering the compositions comprising iron hemoprotein generally may be found in *Remington's Pharmaceutical Sciences,* Meade Publishing Col., Easton, Pa., latest edition. In a preferred embodiment, the hemoglobin is administered intravascularly. The amount of iron hemoprotein administered, the effective amount, is an amount sufficient to bind to substantially all of the nitric oxide present, thus removing from nitric oxide from circulation. Such an effective amount is generally in a range of from about 0.1 g/kg body weight to about 10 g/kg body weight.

The following examples are presented to illustrate a best mode and preferred embodiments of the present invention and are not meant to limit the claimed invention unless otherwise specified.

EXAMPLE 1

Abrogation of Blood Pressure Decline

Experiments were carried out on conditioned mongrel dogs weighing 23∞kg. Animal care was in accordance with the recommendations of the American Association for Accreditation of Laboratory Animal Care and met all standards prescribed by the *Guide for the Care and Use of Laboratory Animals* (Committee on Care and Use of Laboratory Animals (1978) *Guide for the Care and Use of Laboratory Animals* (Natl. Inst. Health, Bethesda, Md.) DHEW Publ. No. (NIH) 78–83.

The dog was fasted overnight before the day of the experiment and was anesthetized with pentobarbital (25 mg/kg, i.v.), orotracheally intubated and ventilated with a Harvard pump at a nominal rate of 12 breaths per minute and a tidal volume of 15 ml/kg. The dog was instrumented with a cordis for the introduction of a Swan-ganz catheter for measurement of central venous and pulmonary arterial pressures as well as an arterial line for continuous blood pressure monitoring via a computer driven analog to digital processor.

After the blood pressure and heart rate was established, endotoxin was administered to the dog as a bolus injection (50 µg/kg, i.v. In 10 ml DABS. After the onset of hypotension, a rapid infusion of 50 ml hemoglobin (5.0 g commercially available bovine hemoglobin/100 ml) over 20 seconds was administered by a central venous catheter. Cardiovascular changes were monitored for an additional 12 hrs. after hemoglobin administration.

A tracing depicting endoxtin-induced hypotension, its inhibition by hemoglobin, and subsequent administration of bovine serum albumin (5 grams) is shown in FIG. 1. Mean arterial blood pressure declined from 160 mm Hg to 70 mm Hg two hours after endotoxin administration. The hemoglobin (HgB) was subsequently administered as an intravenous bolus. The blood pressure drop was abrogated by this administration and the hypotension was partially reversed. This effect lasted approximately 45 minutes before the blood pressure decline resumed. The subsequent decline was only slightly influenced by the administration of 5 grams of bovine serum albumin (BSA). On repetition of this experiment, substantially the same results were obtained.

EXAMPLE 2

Binding of NO by Myoglobin

Nitric oxide formation by endothelial cell cytosol was measured by a novel kinetic 96-well microplate assay. The assay is based on the capture of NO by $Fe^{2+}$-myoglobin (Mb) which is subsequently oxidized to $Fe^{3+}$-myloglobin. The process of heme oxidation was continuously measured in a kinetic microplate reader (Molecular Devices, Menlo Park, Calif.) as the rate of change in $OD_{405}$-$OD_{650}$. Data points were collected from all 96 wells every 16 sec. for 30 minutes at 25° C. with shaking prior to each OD measurement. The slope of the best fit regression line (OD/min) was used to calculate the rate of NO-synthesis. OD/min measurements were converted to pmoles NO/min by dividing by the increase in $OD_{405}$-$OD_{650}$ measured upon complete oxidation of 1 pmole of reduced Mb with a 10-fold molar excess of potassium ferricyanide. Under the conditions employed, the efficiency of NO capture by Mb approached 100%; neither doubling nor halving the concentration of Mb influenced the Mb oxidation rate. All samples contained 5–30 µl of endothelial cell cytosol (1–6 mg protein/ml) and final concentrations of 5 µM Mb, 500 µM L-arginine, 500 µM NADPH and 80 Mm TRIS, pH 7.6.

$Fe^{2+}$-Myoglobin Preparation: 2 mM myoglobin (from horse skeletal muscle, Sigma) was reduced with a sodium dithionite and immediately applied to a Sephadex G-25 column, followed by elution with 50 Mm TRIS buffer, Ph 7.6. Mb was aliquoted and stored at −70° C. for up to 2 months prior to use. The usefulness of this iron hemoprotein for nitric acid removal is thus clearly shown.

Various references are cited above, the disclosures of which are incorporated in pertinent part by reference herein for the reasons cited.

The invention described and claimed herein is not to be limited in scope by the specific embodiments disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

What is claimed is:

1. A method for treating a patient with a pathogenic syndrome caused by nitric oxide overproduction, the method comprising: administering to said patient an amount of an iron hemoprotein effective to reduce nitric oxide levels.

2. The method of claim 1 where the iron hemoprotein is hemoglobin or myoglobin.

3. The method of claim 1 where the amount is from 0.1 to 10 g/kg body weight.

4. The method of claim 1 where the administering is intravascular.

5. The method of claim 1 where the syndrome is systematic hypotension.

6. A method of reducing intravascular nitric oxide levels in an animal, the method comprising intravascularly administering to said animal an iron hemoprotein in an amount effective in reducing said levels.

7. The method of claim 6 where the iron hemoprotein is hemoglobin or myoglobin.

8. The method of claim 6 where the amount is from 0.1 to 10 g/kg body weight.

9. A method for prohylaxis of a patient's systemic hypotension induced by nitric oxide overproduction, the method comprising administering a prophylactically effective amount of an iron hemoprotein to said patient.

10. The method of claim 9 where the iron hemoprotein is hemoglobin or myoglobin.

11. The method of claim 9 where the amount is from 0.1 to 10 g/kg body weight.

12. A method or treatment of systemic hypotension in a patient caused by vasodilation comprising intravascularly administering an amount of an iron hemoprotein sufficient to bind or oxidize intravascular nitric oxide.

13. The method of claim 12 where the iron hemoprotein is hemoglobin or myoglobin.

14. The method of claim 12 where the amount is from 0.1 to 10 g/kg body weight.

15. The method of claim 12 where the vasodilation is induced by treatment with a cytokine.

16. The method of claim 15 where the cytokine is tumor necrosis factor, interleukin-1, or interleukin-2.

* * * * *